United States Patent [19]

Kaufman

[11] 4,294,847

[45] Oct. 13, 1981

[54] 8-AMINOALKYL-4-ALKYLISOPSORALENS

[75] Inventor: Kurt D. Kaufman, Kalamazoo, Mich.

[73] Assignee: Thomas C. Elder, Inc., Hamilton, Ind.

[21] Appl. No.: 173,384

[22] Filed: Jul. 29, 1980

[51] Int. Cl.³ .................. C07D 493/04; A61K 31/365
[52] U.S. Cl. .............................. 424/279; 260/343.21; 260/326 D
[58] Field of Search .................... 260/343.21; 424/279

[56] References Cited

U.S. PATENT DOCUMENTS 4,235,781  11/1980  Kaufman ........................ 260/343.21

OTHER PUBLICATIONS

Hearst et al., Chem. Abst., vol. 87, 1977, 87:78962f.
Bardin et al., Chem. Abst., 84:160136m.
Kawase et al., Chem. Abst., 89:129432j.

*Primary Examiner*—Henry R. Jiles
*Assistant Examiner*—Jane T. Fan
*Attorney, Agent, or Firm*—Gordon W. Hueschen

[57] ABSTRACT

The invention relates to 8-aminoalkyl-4-alkylisopsoralens, especially 8-aminomethyl-4-methylisopsoralen, having enhanced photosensitizing activity, especially oral and topical activity, pharmaceutical compositions thereof, and method of effecting photosensitization therewith.

10 Claims, No Drawings

8-AMINOALKYL-4-ALKYLISOPSORALENS

BACKGROUND OF INVENTION

1. Field of Invention

Chemical compounds, photochemotherapy, compounds having enhanced photosensitizing activity for use in photochemotherapy.

2. Prior Art

Psoralens have been used for years as dermal photosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in a Psoralite (TM) apparatus. A high percentage of remissions of this disease have been effected in such manner.

The effectiveness of a psoralen for such uses and for such purpose has in the past been related solely to its ability to produce erythema upon the skin upon irradiation. Psoralens also have other uses, and their uses, as well as underlying rationale and theory, are partially elucidated in U.S. Pat. Nos. 4,124,598 and 4,130,568, and are otherwise well-known in the art from various preexisting publications.

Rather recently, it has been found that the erythema, produced upon the skin of a patient or animal upon irradiation with ultraviolet light "A" in a so-called PUVA evaluation or application, after administration of psoralen to the subject, is associated with the linear structure of psoralens, which makes it possible for psoralens to engage in photocycloaddition reactions with double bonds of pyrimidine bases of macromolecules, such as present in the complementary strands of DNA (deoxyribonucleic acid), in a manner such that either only one double bond of the psoralen compound reacts so as to form monofunctional adducts, or that two double bonds of the psoralen compound react so as to produce two (2) cycloadditions with two (2) separate molecules of the pyrimidine base, as present in the complementary strands of DNA, thereby forming an interstrand cross-linkage. Such interstrand cross-linkages occur in photoreactions between highly erythematic psoralens and DNA. On the other hand, some psoralens, because of their angular structure, can engage, for geometric reasons, only one of the two photoreactive sites, thus effecting a single cycloaddition to only one of the two complementary strands of DNA. In other words, psoralen compounds in the photoreaction with DNA can form either or both monofunctional and bifunctional adducts, and this capacity varies with the type of psoralen compound involved, some compounds forming essentially only monofunctional adducts, whereas other compounds form solely or a preponderance of bifunctional adducts or interstrand cross-linkages. The ability or capacity to form only monofunctional and not bifunctional adducts, or at least minimization of bifunctional cycloaddition or bifunctional adduct formation, is now considered desirable from the standpoint that the consequences deriving from bifunctional damage are considered to be more serious from a biological repair standpoint than the consequences deriving from monofunctional cycloaddition or adduct effects. This means at least that it is no longer necessary that a compound exhibit strong bifunctional effects, as evidenced by a high degree of erythema in usual test procedures, but that it is enough that it produce monofunctional adducts or a single cycloaddition without interstrand cross-linkage to DNA. Such compounds as produce monofunctional adducts only, or at least in preponderance, have nevertheless been found effective in the treatment of psoriasis and in producing other desirable effects, even though they do not cause interstrand cross-linkages. Further, psoralens have been found to possess reactivity with ribonucleic acids (RNA), and accordingly the new psoralen compounds find use in the study of secondary structures of nucleic acids, as inhibitors of RNA replication, in the inactivation of viruses, as well as in the photochemotherapy of psoriasis, all important uses.

The standard tests and test procedures, and their significance, are fully elucidated in the following publications: F. Dall'Acqua, S. Marciani, G. Rodighiero; Interstrand cross-linkages occurring in the photoreaction between psoralen and DNA. FEBS letters 9, 121 (1970); F. Dall'Acqua, S. Marciani, L. Ciavatta, G. Rodighiero: Formation of interstrand cross-linkings in the photoreactions between furocoumarins and DNA. Zeitschrift Naturforsch. 26b, 561 (1971); Baccichetti et al., Z. Naturforsch. 34c. 811–814 (1979); Bordin et al., Biochimica et Biophysica Acta 447, 249–259 (1976); Baccichetti et al., Experientia 35, 183 (1979); and see U.S. Pat. Nos. 4,124,598 and 4,130,568, as well as Hearst et al., Nucleic Acids Res. 1977, 4(5), 1339–1347; Isaacs et al., Biochemistry 1977, 16(6), 1058–1064; Shen et al., J. Mol. Biol. 1977, 116(4), 661–679; and Johnson et al., Science 1977, 197(4306), 906–908.

The compounds of the present invention, then, which possess the characteristic, when employed in PUVA therapy, of forming only monofunctional adducts, or essentially so, thus finding employment and use in the foregoing manners, particularly in the photochemotherapy of psoriasis, should be welcome additions to the physicians' armamentarium of useful drugs.

OBJECTS OF THE INVENTION

It is an object of the invention to provide novel isopsoralen compounds. It is a further object to provide novel isopsoralen compounds of unique structure which have beneficial or enhanced characteristics when compared with psoralen compounds of different structure. It is an additional object to provide novel isopsoralen compounds having beneficial or enhanced photosensitizing characteristics in accord with the foregoing stated criteria. It is a still further object to provide novel isopsoralen compounds having beneficial or enhanced photosensitizing characteristics, relatively low toxicity, and of structure differing essentially from known psoralen compounds, the beneficial properties of which could not be predicted on a basis of known structure-activity relationships. Still other objects will be apparent to one skilled in the art and still additional objects will become apparent hereinafter from the following description and claims.

SUMMARY OF THE INVENTION

The present invention relates to 8-aminoalkyl-4-alkylisopsoralens having beneficial or enhanced photosensitizing activity, especially oral and topical activity, as well as low toxicity, when compared with psoralens of different structure. It is particularly concerned with 4-loweralkyl-8-primaryaminoloweralkylisopsoralens, particularly 4-loweralkyl-8-aminomethylisopsoralens, and especially 4-methyl-8-aminomethylisopsoralen and salts thereof. It is to be noted that the compounds of this invention have no 8 carbon atoms methyl or methoxy substituent as in the prior art compounds trisoralen (4,5′, 8-trimethylpsoralen), 8-methoxypsoralen, or the compounds of U.S. Pat. Nos. 4,124,598 or 4,130,558. No. 4′ carbon atom substituent is essential, as in U.S. Pat. No. 4,124,598. An 8-aminoloweralkyl group is uniquely present, however, together with the unique isopsoralen ring, both of which are absent from the aforementioned reference compounds. These new compounds are characterized by excellent photosensitization activity according to various of the aforesaid criteria, as well as relatively low toxicity.

The compounds of the invention have the formula:

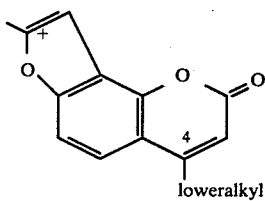

loweralkyl 4-loweralkyl-8-primaryaminoloweralkylisopsoralen, wherein loweralkyl is preferably methyl, which may otherwise be referred to as 4-loweralkyl-5′-aminoalkylisopsoralen or 4-loweralkyl-5′-aminoalkylangelicin, the 8 or 5′ carbon atom being designated by an asterisk.

DETAILED DESCRIPTION OF THE INVENTION

The following preparations and Examples are given by way of illustration only.

Starting 4,8-dialkylisopsoralens and their method of preparation are known. K. D. Kaufman, J. Org. Chem. 26, 117 (1961), (Ref. 2). Their preparation is from a known 7-allyloxy-4-alkylcoumarin via a known 8-allyl-7-hydroxy-4-alkylcoumarin, having a known method of preparation. W. Baker and O. M. Lothian, J. Chem. Soc. 628 (1935) (Ref. 1). According to the invention, variations in the alkyl groups in the end product are effected by variations in the starting 4,8-dialkylisopsoralen, other reaction steps remaining the same.

Thin layer chromatography (TLC) was carried out on Analtech, Silica Gel$_{254}$ 250 micron, glass-backed, slides using benzene: 2-butanone: 17:3. NMR were run on a Perkin Elmer Model R-24B. All melting points are uncorrected.

4-METHYL-8-AMINOMETHYLISOPSORALEN

7-Allyloxy-4-methylcoumarin

7-Hydroxy-4-methylcoumarin (70.00 g, 0.397 mol), anhydrous K$_2$CO$_3$ (140 g, 1.01 mol), and allyl bromide (100 ml, 1.15 mol) were added to 2.0 L of reagent grade acetone. The milky mixture was refluxed for sixteen hours with overhead stirring, allowed to cool to room temperature, and filtered. Solids were washed once with reagent grade acetone (150 ml.), the filtrate and wash combined, and the resulting combined filtrate concentrated to dryness with a rotary evaporator to obtain 7-allyloxy-4-methylcoumarin (84.2 g, 98% yield). The crude product melted at 100.0°–101.5° C. (lit. 1 101° C.), showed only one spot in TLC, and was used in the next step.

8-Allyl-7-hydroxy-4-methylcoumarin

Crude 7-allyloxy-4-methylcoumarin (83.5 g, 0.381 mol) was dissolved in 250 ml of diethyl aniline with heating, and the solution was allowed to reflux for two hours. After the solution had cooled and some product had precipitated, petroleum ether (b.p. 30°–60° C., 760 ml) was added. A brown precipitate formed and was collected by filtration, washed with three small portions of petroleum ether, and dried in vacuo to obtain the crude product. Recrystallization from 600 ml of 95% EtOH gave the pure product (53.5 g, 74% recovery, 65% yield) of mp 192.5°–195.0° C. (lit. 193°–194° C.). TLC showed only a single spot.

7-Acetoxy-4-methyl-8-allylcoumarin

A solution of 8-allyl-7-hydroxy-4-methylcoumarin (61.0 g, 0.282 mol) and a few pinches of anhydrous sodium acetate in boiling acetic anhydride (480 ml.) was allowed to relux for four hours with magnetic stirring. The cooled brown mixture was then poured into water (1750 ml.) with magnetic stirring. The mixture was allowed to stir for half an hour. A brown precipitate was collected by filtration, washed with water, and dried in vacuo to obtain 7-acetoxy-4-methyl-8-allylcoumarin (68.5 g. 94% yield), mp. 98.8°–99.8° C. (lit.[2] 87°–87.5° C.).

7-Acetoxy-4-methyl-8-(2′,3′-dibromopropyl) coumarin

To a stirred solution of 7-acetoxy-4-methyl-8-allylcoumarin (68.3 g, 0.264 mol) dissolved in chloroform (300 ml.) was added dropwise a solution of bromine (42.27 g, 0.264 mol) in chloroform (150 ml.). After all of the bromine-chloroform solution was added, the mixture was allowed to stir for five minutes and then the chloroform was removed with a rotary evaporator to obtain crude 7-acetoxy-4-methyl-8-(2′, 3′-dibromopropyl)coumarin (108.1 g, 98% yield), mp. 145°–148° C. (lit.[2] 156°–157° C.).

4,8-Dimethylisopsoralen

A solution of sodium (29.8 g, 1.296 mol) in dry, absolute ethanol (1400 ml.) was added to 7-acetoxy-4-methyl-8-(2′, 3′-dibromopropyl)coumarin (108.1 g, 0.259 mol). The mixture was allowed to reflux for one hour and 45 minutes with magnetic stirring. The cooled mixture was poured into a mixture of ice (2800 g) and 3.5% HCl (2800 ml.) and stirred. A yellow precipitate was collected by filtration, washed first with three portions (600 ml.) of 5% NaOH, second with one portion (600 ml.) of 3.5% HCl, third with three portions (600 ml.) of water, and then dried in vacuo to obtain crude 4,8-dimethylisopsoralen (48.6 g, 87.6% yield, mp. 160°–174° C.). Recrystallization from 95% ethanol (1500 ml.) gave the pure product (33.7 g, 68% recovery, 61% yield) mp. 176°–178° C. (lit.[2] 182°–183° C.).

4-Methyl-8-bromomethylisopsoralen

To a solution of 4,8-dimethylpsoralen (31.70 g, 0.148 mol) dissolved in boiling CCl$_4$ (3200 ml.) was added N-bromosuccinimide (26.34 g, 0.148 mol) and dibenzoyl peroxide (3.58 g, 0.0148 mol). The refluxing mixture was monitored with KI starch paper and a negative test was obtained after three hours. The boiling mixture was then filtered and the hot, yellow filtrate was allowed to cool and held at zero degrees Centigrade for 48 hours.

Yellow crystals were collected by filtration, washed with cold CCl$_4$ (200 ml.), taken up in CHCl$_3$ (2100 ml.), and extracted with four portions (1500 ml.) of water. The CHCl$_3$ layer was dried over anhydrous MgSO$_4$ and concentrated with a rotary evaporator to give 4-methyl-8-bromomethylisopsoralen (29.7 g, 68% yield), mp. 211°–214° C. Sublimation in vacuo gave a small analytical sample, mp. 215.5°–217.0° C. NMR(CDCL$_3$) $\delta$2.52(s,3, CH$_3$), $\delta$4.61 (s,2,—CH$_2$Br), $\delta$6.25(s,1,C$_3\underline{H}$), $\delta$7.08(s,1,C$_9\underline{H}$), $\delta$7.36(d,1,J=9Hz, C$_6\underline{H}$), $\delta$7.51(d,1,J=8Hz,C$_5\underline{H}$).

Anal. Calcd. for C$_{13}$H$_9$O$_3$Br: C,53.26; H,3.09; Br,27.27. Found: C,53.33; H,3.06; Br,27.20.

8-Phthalimidomethyl-4-methylisopsoralen 8-bromomethyl-4-methylisopsoralen (29.2 g. 99.6 mmol) and potassium phthalimide (22.13 g, 119.0 mmol) were added to dimethylformamide (2340 ml.). After 14 hours at 100° C., the dark brown solution was concentrated on a rotary evaporator to a dark brown paste, washed with three portions (600 ml.) of water and collected by filtration. Recrystallization from glacial acetic acid (900 ml. which was boiled down to 400 ml.) gave 8-phthalimidomethyl-4-methylisopsoralen (24.2 g, 68% yield), mp. 248°–250° C. Sublimation in vacuo gave a small analytical sample, mp. 274°–276° C.

Anal. Calcd. for C$_{21}$H$_{13}$O$_5$N: C,70.19; H,3.65; N,3.90 Found: C,70.13; H,3.68; N,3.68

4-Methyl-8-aminomethylisopsoralen

8-Phthalimidomethyl-4-methylisopsoralen (23.7 g, 66 mmol) and 85% hydrazine hydrate (30.14 ml., 31.04 g. 620mmol) were added in that order to 95% ethanol (2.8 L). The mixture was refluxed for 3.5 hours. A monitor by TLC showed the reaction complete after three hours. The orange solution was concentrated with a rotary evaporator to a yellow precipitate. Saturated aqueous NaHCO$_3$ (500 ml.) was added and the resulting brown solution was extracted with three portions (600 ml.) of CHCl$_3$. The CHCl$_3$ extracts were combined and extracted first with one portion (600 ml.), followed with two portions (200 ml.), of HCl (1F). The HCl extracts were combined, backwashed with CHCl$_3$ (100 ml.) and the solid NaHCO$_3$ was added until a pH of 6. Saturated aqueous NaHCO$_3$ was then added until a pH of 8. A yellow precipitate was collected by filtration and dried in vacuo to give the bicarbonate salt of 4-methyl-8-aminomethylisopsoralen. (13.6 g, mp. 167°–169° C.). Analysis of this material is reported below. The bicarbonate salt was dissolved in HCl (1F, 200 ml.), then NAOH (20%) was added until a pH of 10. A yellow precipitate formed in the aqueous layer and was extracted into CHCl$_3$ with three portions (500 ml.) of CHCl$_3$. The CHCl$_3$ extracts were combined, dried over anhydrous Na$_2$SO$_4$, and rotary evaporated to obtain 4-methyl-8-aminomethylisopsoralen. (8.4 g, 56% yield, mp. 167°–169° C.). Sublimation in vacuo gave a small analytical sample, mp. 167°–169° C. TLC showed only a single spot. NMR(CDCl$_3$) $\delta$1.57(s,2;NH$_2$), $\delta$2.43(s,3,CH$_3$), $\delta$3.98(s,2,CH$_2$), $\delta$6.19(s,1,C$_3\underline{H}$), $\delta$6.80(s,1,C$_9\underline{H}$), $\delta$7.25(d,1,J=Hz,C$_6\underline{H}$), $\delta$7.40(d,1,J=Hz,C$_5\underline{H}$).

Anal. for bicarbonate salt of amine. Cald. for C$_{27}$H$_{24}$N$_2$O$_9$: C, 62.30: H,4.65; N,5.38. Found: C, 62.44; H,4.64; N,5.42.

Anal. for amine. Cald. for C$_{13}$H$_{11}$O$_3$N: C, 68.11; H,4.84; N,6.11. Found: C, 68.17; H,4.82; N,6.05.

4-ETHYL-8-AMINOMETHYLISOPSORALEN

In the same manner as given in the foregoing, but starting from 4-ethyl-8-methylisopsoralen in Step 6 or from 7-allyloxy-4-ethylcoumarin in Step 2, the title compound is produced.

4-PROPYL-8-AMINOMETHYLISOPSORALEN

In the same manner as given in the foregoing, but starting from 4-propyl-8-methylisopsoralen in Step 6 or from 7-allyloxy-4-propylcoumarin in Step 2, the title compound is produced.

4-METHYL-8-(1-AMINOETHYL)ISOPSORALEN

In the same manner as given in the foregoing, but starting from 4-methyl-8-ethylisopsoralen in Step 6 or the selected predecessor intermediate in a previous step, the title compound is produced.

In the same manner as given in the foregoing, other variations in selection of starting materials are productive of still other 4-loweralkyl-8-aminoloweralkylisopsoralens, within the scope of the invention, in which one or both of the loweralkyl groups are varied. As used herein, the term "loweralkyl" comprehends such straight or branched radicals or groups having one to eight carbon atoms, inclusive, preferably one to four carbon atoms, inclusive, such as methyl, ethyl, propyl, isopropyl, butyl, and the like.

When isolating compounds of the invention in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lacetates, citrates, tartrates or bitartrates, and maleates. Other acids are likewise suitable and may be employed if desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

PHARMACOLOGY

The biophotosensitization activity of the compounds of the invention is minimal in the erythemal response test according to the procedure of Pathak and Fitzpatrick, J. Invest. Dermatol., 32, 509–518 (1959), entitled "Bioassay of Natural and Synthetic Furocoumarins (Psoralens)", and usually employed standard modifications thereof. As "biophotosensitization activity" is employed herein, however, as well as "Photochemical sensitivity on the skin of a mammal", and "photosensitizing" or "photosensitizations", as well as "photochemotherapy", the compounds of the invention are active biophotosensitizing agents inasmuch as they produce solely or at best a preponderance of monoaddition or monofunctional addition in the standard tests for DNA photoreactivity, said monofunctional addition being opposed to interstrand cross-linking, as explained in the foregoing. The compounds are thus clearly useful in the further study of reactions and secondary structures of nucleic acids, and as inhibitors of RNA replication, and are indicated for employment in the inactivation of viruses as well as in the photochemotherapy of psoriasis by the PUVA procedure, in which they are found to be equally as effective as numerous previously-employed psoralen compounds, without the production of excessive erythema, if any, which is of course dependent upon numerous factors, such as amount of irradiation employed, dosage of the photosensitizing agent, mode of employment (whether topical or oral), and individual skin sensitivities of the mammal subjected to the PUVA therapy, including of course human beings, with respect to which psoriasis is a unique malady. The compounds are accordingly useful for all of the foregoing purposes, but particularly for effecting photochemical sensitivity on the skin of a mammal, these terms as employed herein not being restricted to the production of erythema thereon. They are effective both orally and topically, and the method of effecting photochemical-sensitivity on the skin of a mammal merely comprises the step of orally or topically administering to the said mammal an effective photosensitizing dose of a compound of the invention. When the subject is then exposed to ultraviolet radiation, more particularly ultraviolet "A", in the non-burning range, monofunctional adducts are formed and psoriasis is mitigated in human patients, as aforesaid. Other uses of the compounds of the present invention are also set forth in the foregoing.

The pharmaceutical compositions according to the present invention are suitable for use in effecting photochemical sensitivity on the skin of a mammal, particularly a human patient or subject, and comprise an effective amount of a compound of the invention in association with a pharmaceutically-acceptable carrier or diluent. Such compositions are well-known in the art, and reference may again be made to U.S. Pat. Nos. 4,124,598 and 4,130,568 for representative examples and disclosure concerning the same. The procedure for preparation of such compositions is totally conventional in the art. For oral treatment of psoriasis, the active ingredient is generally formulated in tablets or in gelatin capsules. In such case the diluent may, if desired, be eliminated, although it is generally present. For topical application, solutions or ointments may be prepared and employed. These may be formulated with any one of a number of pharmaceutically-acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 10 mg. to about 50 mg. per kg. of body weight, with a dose in the neighborhood of about 20 mg. per kg. generally being preferred. Such administration and selection of dosage and unit dosage will of course have to be determined according to established medical principles and under the supervision of the physician in charge of the PUVA therapy involved. For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carriers of the type already mentioned.

It is to be understood that the invention is not to be limited to the exact details of operation or exact compounds, compositions, methods, or procedures shown and described, as obvious modifications and equivalents will be apparent to one skilled in the art.

I claim:
1. 4-loweralkyl-8-primaryaminoloweralkylisopsoralen or a non-toxic and pharmacologically-acceptable salt thereof.
2. A compound of claim 1 which is 4-loweralkyl-8-aminomethylisopsoralen.
3. A compound of claim 1 which is 4-methyl-8-aminomethylisopsoralen.
4. A compound of claim 1 which is 4-methyl-8-aminomethylisopsoralen bicarbonate salt.
5. The method of effecting photochemical sensitivity on the skin of a mammal comprising the step of orally or topically administering to the said mammal an effective photosensitizing dose of a compound of claim 1.
6. The method of claim 5 wherein the compound is 4-loweralkyl-8-aminomethylisopsoralen.
7. The method of claim 5 wherein the compound is 4-methyl-8-aminomethylisopsoralen.
8. A pharmaceutical composition suitable for use in effecting photochemical sensitivity on the skin of a mammal comprising an effective amount of a compound of claim 1 and a pharmaceutically-acceptable carrier or diluent.
9. The composition of claim 8 wherein the compound is 4-loweralkyl-8-aminomethylisopsoralen.
10. The composition of claim 8 wherein the compound is 4-methyl-8-aminomethylisopsoralen.

* * * * *

UNITED STATES PATENT AND TRADEMARK OFFICE
CERTIFICATE OF CORRECTION

PATENT NO. : 4,294,847

DATED : October 13, 1981

INVENTOR(S) : Kurt D. Kaufman

It is certified that error appears in the above—identified patent and that said Letters Patent is hereby corrected as shown below:

Col. 2, line 56; "of structure" should read -- of a structure --
Col. 3, line 6; "atoms" should read -- atom --
Col. 3, line 9; "4,130,558" should read -- 4,130,568 --
Col. 3, approximately line 20 (top left corner of the formula) insert -- aminoloweralkyl --
Col. 5, line 45; "the" should read -- then --
Col. 6, line 36; "lacetates" should read -- lactates --

Signed and Sealed this

Ninth Day of February 1982

[SEAL]

Attest:

GERALD J. MOSSINGHOFF

Attesting Officer   Commissioner of Patents and Trademarks